United States Patent [19]

Härri et al.

[11] 4,215,199

[45] Jul. 29, 1980

[54] ANTIBIOTIC PRODUCTION

[75] Inventors: Eugen Härri, Therwil; Artur Rüegger, Bottmingen, both of Switzerland

[73] Assignee: Sandoz Ltd., Basel, Switzerland

[21] Appl. No.: 912,180

[22] Filed: Jun. 5, 1978

Related U.S. Application Data

[60] Division of Ser. No. 781,722, Mar. 28, 1977, Pat. No. 4,117,118, which is a continuation-in-part of Ser. No. 721,836, Sep. 9, 1976, which is a continuation-in-part of Ser. No. 604,941, Aug. 15, 1975, abandoned, which is a continuation-in-part of Ser. No. 528,474, Nov. 29, 1974, abandoned.

[51] Int. Cl.$^2$ ............................................. C12P 21/04
[52] U.S. Cl. ..................................... 435/71; 435/911; 435/945; 435/803
[58] Field of Search ............................ 195/81; 435/71

[56] References Cited

FOREIGN PATENT DOCUMENTS

| | | |
|---|---|---|
| 155753 | 11/1974 | Switzerland . |
| 155754 | 11/1974 | Switzerland . |
| 1006724 | 3/1962 | United Kingdom . |

OTHER PUBLICATIONS

Mirrington et al., Aust. J. Chem. 19, 1265–1284, (1966).
Barth et al., Folio Microbial 19, 507–511, (1974).
Gams, Persoonia, vol. 6 part 2, 185–191, (1971).
Ruegger et al., Helv. Chim. Acta., pp. 1–32, vol. 59 (1976).
Petcher et al., Helv. Chim. Acta, vol. 59 (1976).
Dreyfuss et al., European J. Appl. Microbiology, pp. 1–14, (1976).
Evans et al., Trans. Br. mycol. Soc. 49 (3), 563–567, (1966).
Handbook of Microbiology, vol. III, edited by Laskin et al., CRC Press Inc., pp. 308 & 309, (1974).

*Primary Examiner*—Alvin E. Tanenholtz
*Attorney, Agent, or Firm*—Gerald D. Sharkin; Robert S. Honor; Thomas O. McGovern

[57] ABSTRACT

This invention provides new antibiotics produced by cultivating a strain of the fungus species, *Cylindrocarpon lucidum* Booth or *Tolypocladium inflatum* Gams in contact with a nutrient medium, the antibiotics being useful anti-inflammatory and immunosuppressive agents.

9 Claims, 6 Drawing Figures

ANTIBIOTIC PRODUCTION

This is a division of application Ser. No. 781,722, filed Mar. 28, 1977 which issued as U.S. Pat. No. 4,117,118 on Sep. 26, 1978, which in turn is a continuation-in-part of Ser. No. 721,836, filed Sept. 9, 1976, which in turn is a continuation-in-part of Ser. No. 604,941, filed Aug. 15, 1975, now abandoned, which in turn is a continuation-in-part of Ser. No. 528,474, filed Nov. 29, 1974, now abandoned.

The present invention relates to the new antibiotics hereinafter referred to as S 7481/F-1 and S 7481/F-2 and processes for the production of these antibiotics.

Figure 1:
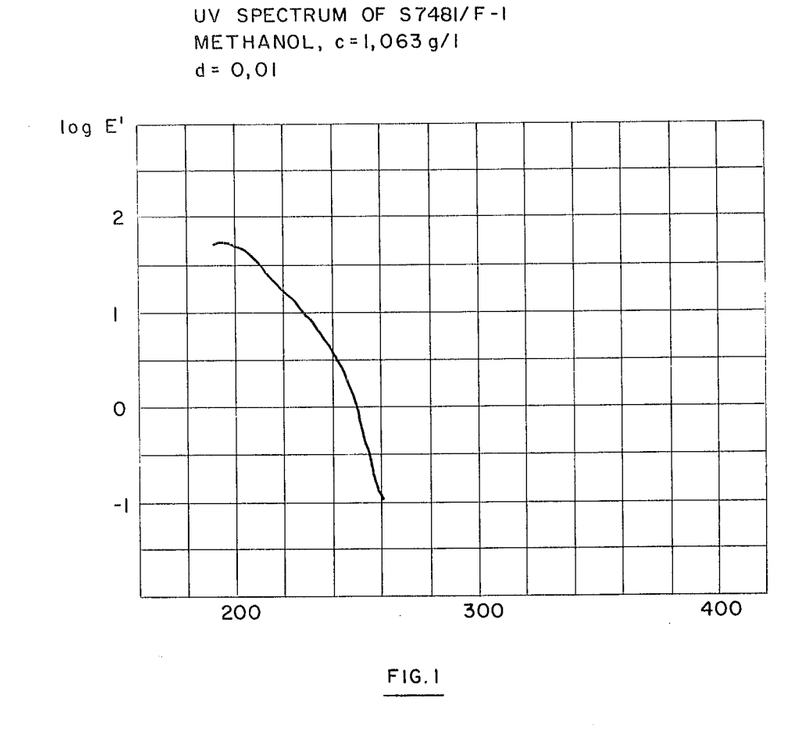
Figure 2:
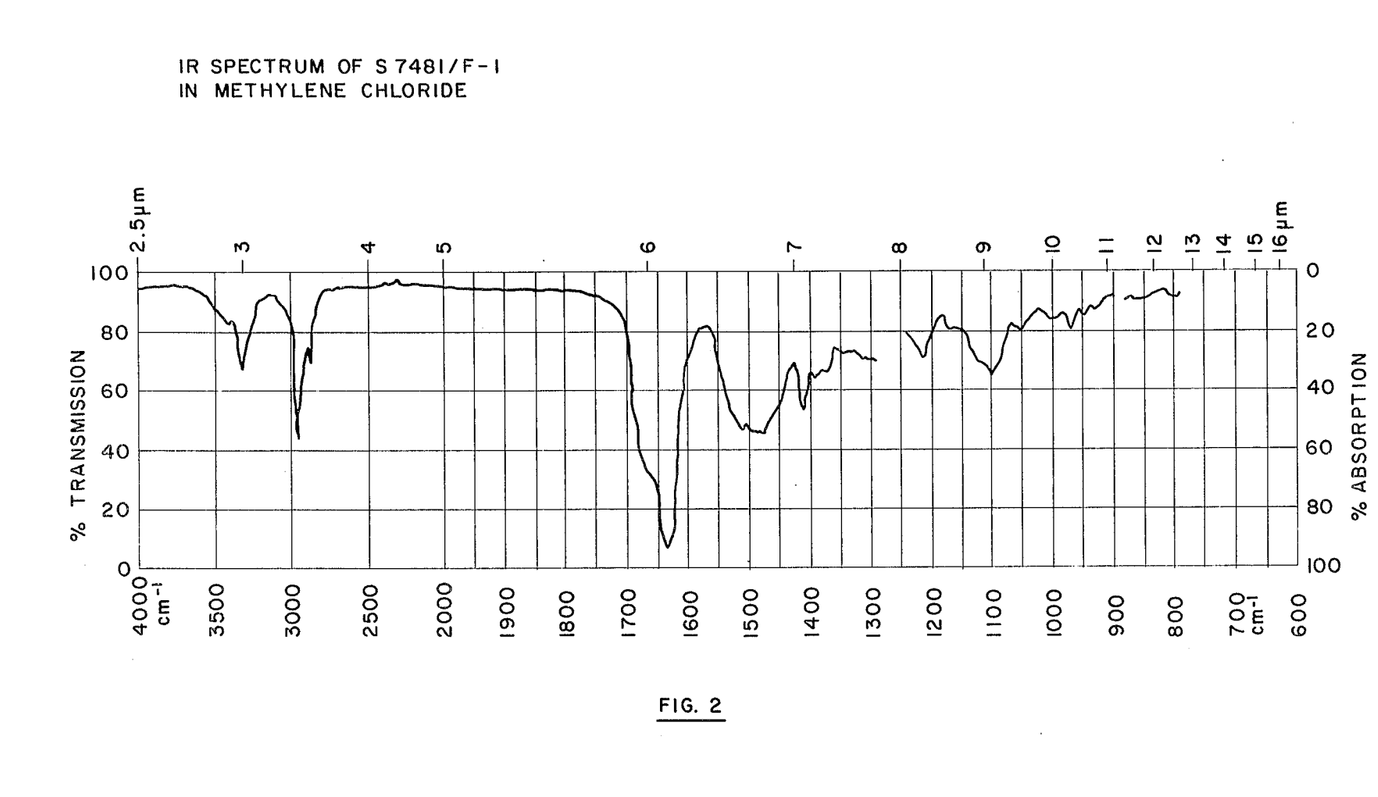
Figure 3:
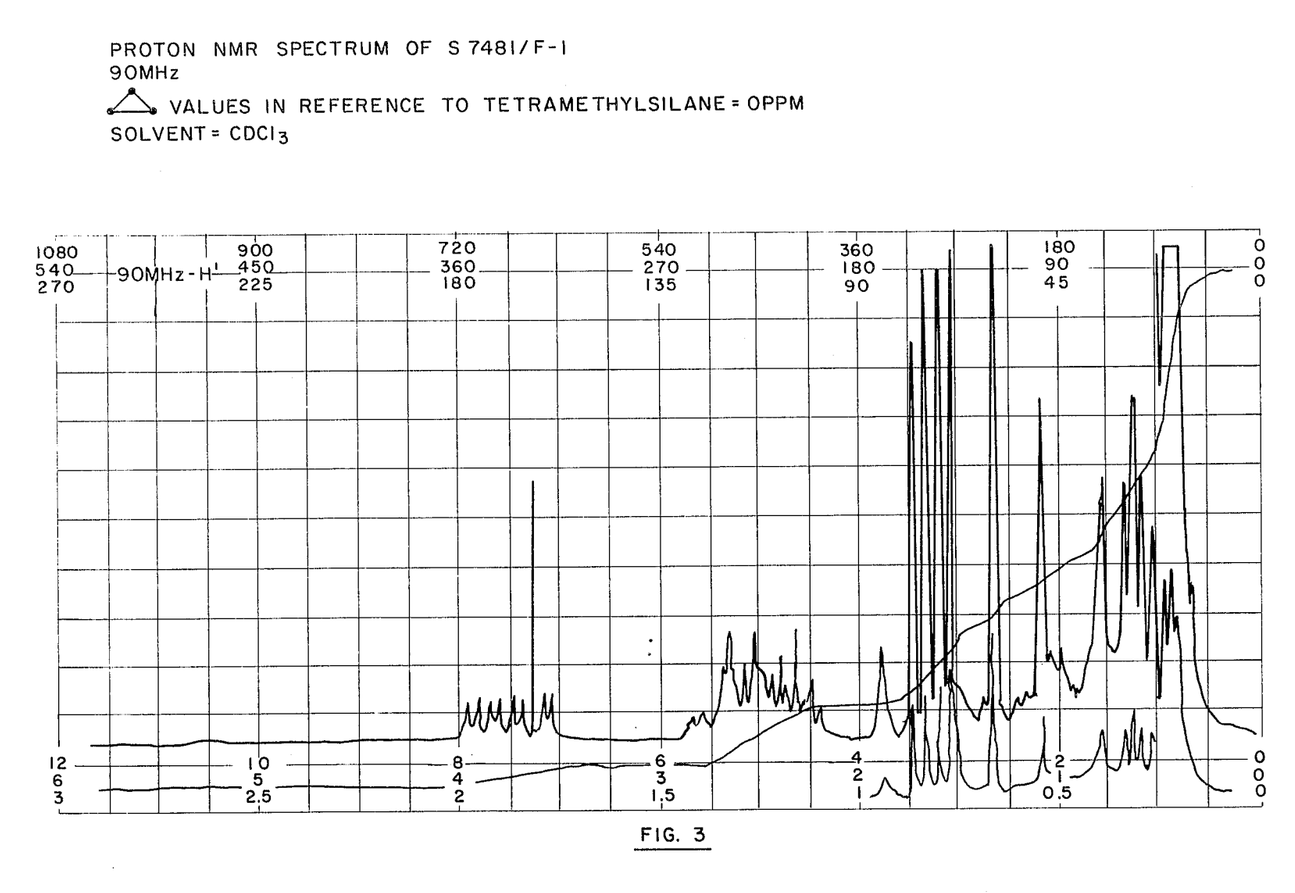
Figure 4:
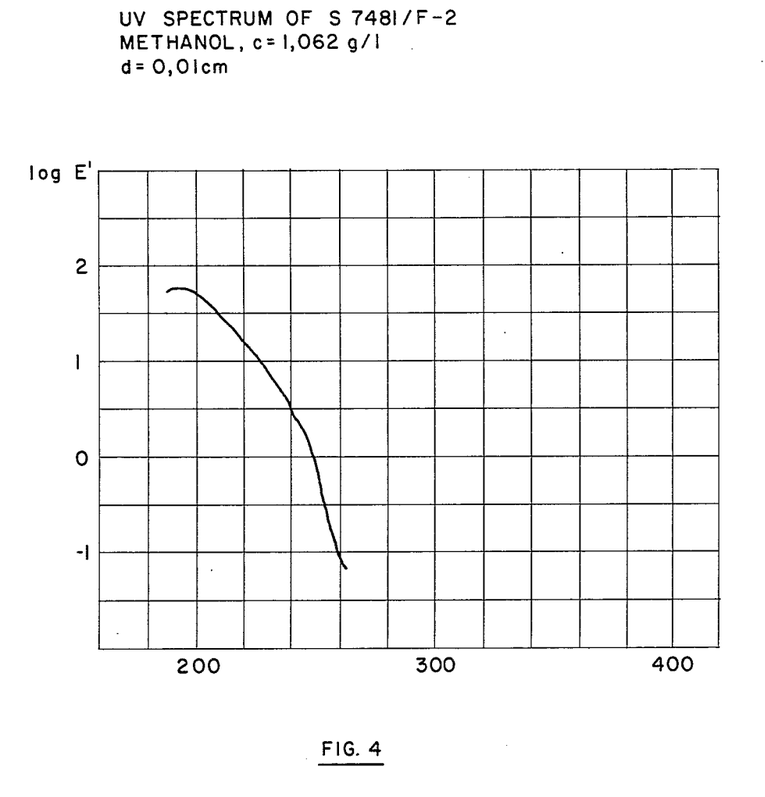
Figure 5:
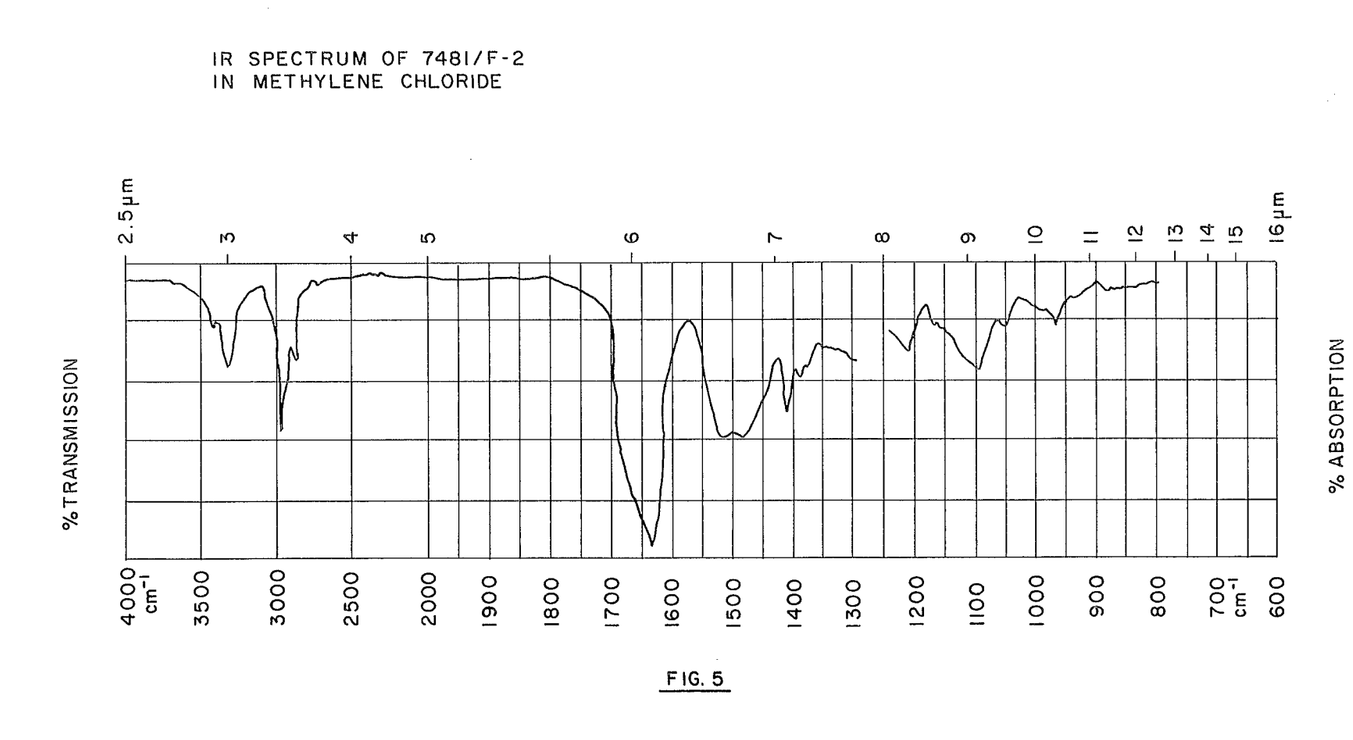
Figure 6:
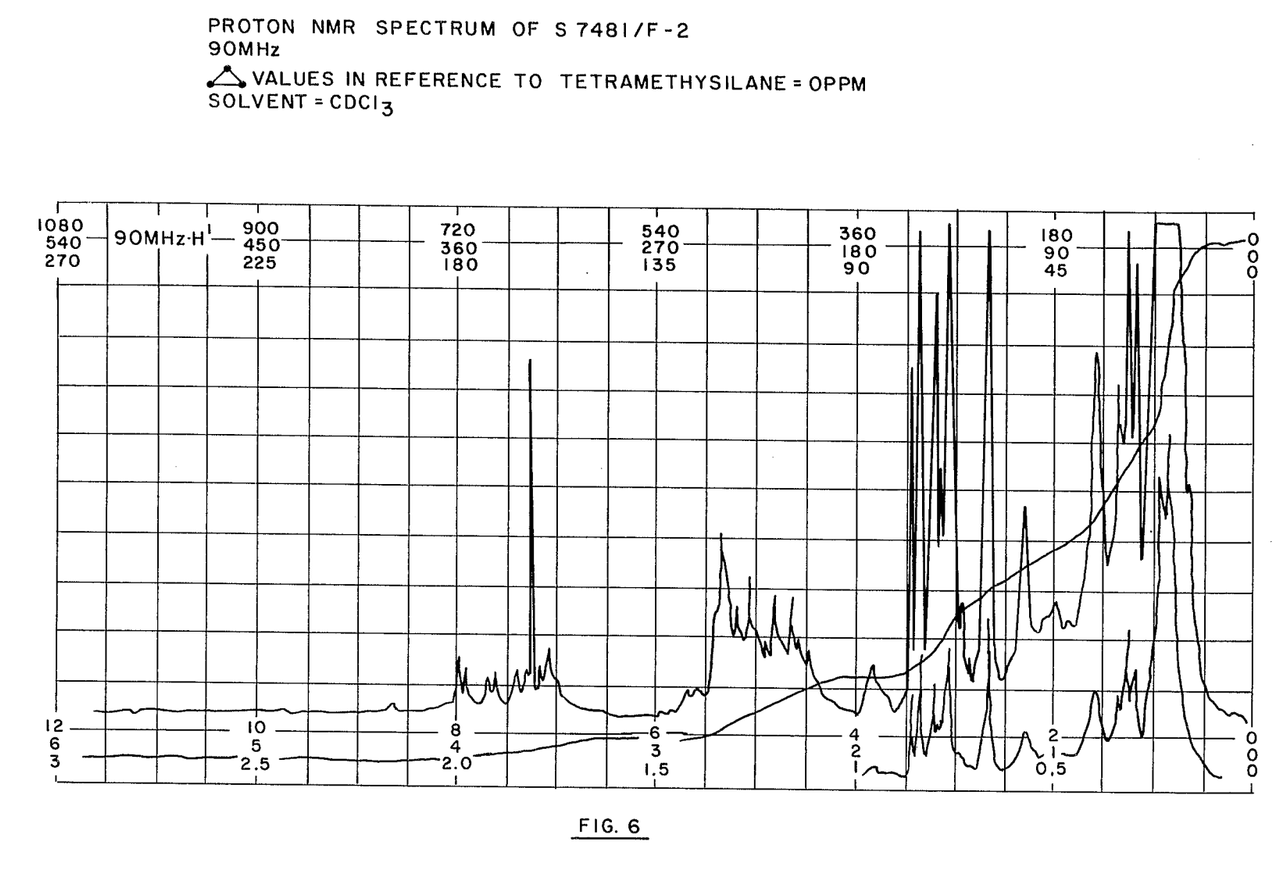

The invention provides a process for the production of antibiotic S7481/F-1, S7482/F-2, or S7481/F-1 and S7481/F-2, which comprises cultivating a S7481/F-1; S7481/F-2, or S7482/F-1 and S7481/F-2 producing strain of the fungus species, *Cylindrocarpon lucidum* Booth or *Trichoderma polysporum* (Link ex Pers.) Rifai (now referred to as *Tolypocladium inflatum* Gams), in contact with a nutrient medium and isolating S7481/F-1; S7481/F-2 or S7481/F-1 and S7481/F-2, antibiotic S7481/F-1 having the following characteristics when in amorphous form:
colourless powder; M.P. 148°–151° C. (decomp.);
$[\alpha]_D^{20} = -236°$ (CHCl$_3$; c=0.5);
U.V. Spectrum [CH$_3$OH; c=1.063 g/l; d=0.01 cm] as shown in FIG. 1 of the accompanying drawings;
I.R. Spectrum [CH$_2$Cl$_2$] as shown in FIG. 2 of the accompanying drawings;
Proton N.M.R. Spectrum [90 MHz; CDCl$_3$] as shown in FIG. 3 of the accompanying drawings;
Carbon-13 N.M.R. Spectrum [250 mg in 1.5 ml CDCl$_3$; sweep width 6000 MHz] as shown in accompanying Table;
High resolution mass spectrum [ion acceleration 4 kv; temperature ion source 290° C.; pressure $5.10^{-6}$ mm Hg] peak of highest mass=m/e 1183.831 [±0.004] corresponding to C$_{62}$H$_{109}$N$_{11}$O$_{11}$ recognisable as product of elimination of water from C$_{62}$H$_{111}$N$_{11}$O$_{12}$;
Elementary analysis C 61.8, H 9.4, N 13.0, O 15.7% in agreement with empirical formula C$_{62}$H$_{111}$N$_{11}$O$_{12}$; and release of amino acids alanine, α-aminobutyric acid, N-methylleucine, N-methylglycine and valine on reaction with 6 N aqueous hydrochloric acid at reflux; and antibiotic S7481/F-2 having the following characteristics when in amorphous form:
Colourless powder; M.P. 127°–130° C. (decomp.);
$[\alpha]_D^{20} = -243°$ (CHCl$_3$, c=0.5);
U.V. Spectrum [CH$_3$OH; c=1.062 g/l; d=0.01 cm] as shown in FIG. 4 of the accompanying drawings;
I.R. Spectrum [CH$_2$Cl$_2$] as shown in FIG. 5 of the accompanying drawings;
Proton N.M.R. Spectrum [90 MHz; CDCl$_3$] as shown in FIG. 6 of the accompanying drawings;
High resolution mass Spectrum [ion acceleration 4 kv; ion source temperature 290° C.; pressure $5.10^{-6}$ mm Hg] peak of highest mass m/e 1169.815 (±0.006) corresponding to C$_{61}$H$_{107}$N$_{11}$O$_{11}$, the product of water elimination from C$_{61}$H$_{109}$N$_{11}$O$_{12}$; and
Elementary analysis found C 61.7; H 9.1, N 13.1, O 16.5% in agreement with empirical formula C$_{61}$H$_{109}$N$_{11}$O$_{12}$.

The structure of S 7481/F-1 is as follows:

The structure of S7481/F-2 is as follows:

S-7481/F-1 and S-7481/F-2 have been designated as Cyclosporins A and B, respectively. The chemical properties and isolation of Cyclosporin A are described in the following articles:

A. Ruegger, M. Kuhn, H. Lichti, H-R. Loosli, R. Hugenin, C. Quiquerez, and A.von Wartburg, Helv. Chim. Acta. 1976, Vol 59.

T. J. Petcher, H. P. Weber and A. Ruegger, Helv. Chim. Acta. 1976, Vol 59

M. Dreyfuss, E. Härri, H. Hofmann, H. Kobel, W. Pache and H. Tscherter, European J. of Appl. Microbiology, 1976, the contents of which are incorporated herein by reference.

When the strain is a *Cylindrocarpon lucidum* Booth strain, this is preferably the strain NRRL 5760 described hereinafter, or an obvious taxonomical equivalent thereof, or a mutant or variant thereof.

When the strain is a *Tolypocladium inflatum* Grams Rifai strain, this is preferably the strain NRRL 8044 described hereinafter, or an obvious taxonomical equivalent thereof, or a mutant or variant thereof.

The invention also provides the antibiotics S7481/F-1 and S7481/F-2 as defined above and described herein.

The invention also provides fermentation liquors produced by cultivating either strain NRRL 5760 or strain NRRL 8044, or an obvious taxonomical equivalent thereof on a synthetically produced nutrient medium.

The new strain of the fungus species *Cylindrocarpon lucidum* Booth employed in the process of the invention was isolated from a soil sample found in the State Wisconsin, USA, and a specimen of said strain has been deposited with the United States Department of Agriculture (Northern Research and Development Division), Peoria, Ill., USA, under the reference NRRL 5760.

In its essential characteristics, the new strain NRRL 5760 of *Cylindrocarpon lucidum* Booth conforms to the original description (C. Booth 1966, The Genus Cylindrocarpon, Mycological Papers No. 104, 21). On potato dextrose agar the strain NRRL 5760 forms neither chlamydospores nor microconidia. However, chlamydospore-like cells of the macroconidia are also lacking. The banana-shaped macroconidia, which are usually partitioned by 3 transverse walls, measure 28–45×4-.8–5.7μ and are, therefore, considerably smaller than indicated in the above mentioned description (45-65-×6-6.5μ). A further important difference lies in the growth rate; while the type should form colonies measuring 1–1.5 cm within 7 days, the strain NRRL 5760 grows to colonies measuring 7–8 cm within the same time, whereby colourless or brown substrate mycelium is formed almost exclusively on potato dextrose agar. The conidiophores with the phialides are formed already after a few days in tight groups and bundles, are branched in a penicillium-like or verticillium-like manner and form macroconidia over a longer period, these macroconidia accumulating as slimy, beige-coloured mass.

The new strain of the fungus species *Tolypocladium inflatum* Gams employed in the process of the invention was isolated from a soil sample found in Norway, and a specimen of said strain has been deposited with the United States Department of Agriculture (Northern Research and Development Division), Peoria, Ill., USA, under the reference NRRL 8044.

The new strain NRRL 8044 of *Tolypocladium inflatum* Gams Rifai grows on a 2% malt extract agar at between 6° and 33° C., the optimum growth is around 24° C., when pure white, superficially velvet-like and unwrinkled colonies, having a diameter of 40–45 mm, are formed within 12 days. However, at the highest temperature permitting a good growth (33° C.), no aerial mycelium, but a very strongly wrinkled colony is formed. With increasing culture temperatures a yellow pigment is increasingly formed on the under side of the colony, this pigment diffusing into the agar at 27° C. and still more pronouncedly at 30°–33° C.

In order to form conidiophores, standing scattered or in tight groups, especially however at the border of the culture vessel, the new strain of *Tolypocladium inflatum* Gams requires 15 to 20 days on malt extract agar at 24° C. The morphology of the conidophore form slightly differs in some of its characteristics from the description of *Trichoderma polysporum* (Link ex Pers.) Rifai (M. A. Rifai 1969, A Revision of the Genus Trichoderma, Mycological Papers No. 116). Thus, the main branch of the conidiophores reaches a diameter of 2.0–3.8μ only, whereas 4–6.3μ are indicated for the species. The phialides of the new strain of *Tolypocladium inflatum* Gams are elongated, especially at the end of their development, this being untypical for this species. Finally, the conidia are somewhat smaller than what is indicated in the description of the species, i.e. 2.0–3.1×1.5–2.0μ, as compared with 2.4–3.8×1.8–2.2μ. The present strain NRRL 8044 of *Tolypocladium inflatum* Gams does not form real chlamydospores under any of the indicated culture conditions.

Following an article by Gams, Persoonia 185 (1971) the new strain fits the description of a species of Trichodermia polysporum reclassified by Gams as "Tolypocladium inflatum".

The new fungus strains NRRL 5760 and NRRL 8044 may be cultivated on various nitrient media containing the usual nutrients for fungi. For example, such strains make use of nitrients usually employed for carbon-heterotropic organisms, e.g. sucrose, glucose, maltose, lactose, starch, malt extract as the carbon source, organic and inorganic nitrogen-containing compounds such as cornsteep, soy peptone, yeast or meat extracts, sodium nitrate, ammonium sulphate, ammonium nitrate, amino acids etc. as the nitrogen source, as well as the usual mineral salts and trace elements.

The new antibiotics S 7481/F-1 and S 7481/F-2 may be produced by
1. inoculating a liquid medium with a conidia or mycelium suspension of the strain NRRL 5760, and incubating the culture for 9 to 13, preferably 11 days, at 24°–30° C. preferably 27° C., and at a pH value of 4.8–8.8, preferably 8.1. This cultivation is effected in penicillin flasks under aerobic conditions by surface culture fermentation,
2. inoculating a liquid medium with a conidia or mycelium suspension of the strain NRRL 8044, and incubating the culture for 11 to 18, preferably 13 days, at 25°–30°, preferably 27° C., and at a pH value of 4.3–6.2, preferably 5.6, in a steel fermenter, while stirring (170 r.p.m.) and aerating (1 liter of air/minute/liter of nutrient solution).

As soon as the maximum amount of antibiotics has been produced, these are obtained from the culture liquor in known manner by extractive and/or adsorptive methods.

One convenient method comprises the extraction of the mycelium obtained from cultivation of the fungus strain NRRL 5760, optionally after previous mechanical comminution, with 90% methanol, subsequent removal of the methanol by evaporation, and repeated extraction of the resulting aqueous mixture with ethylene chloride. The ethylene chloride extract obtained from the culture filtrate may be added to this extract. However, other organic, water-immiscible solvents, e.g. chloroform, ethyl acetate, methylene chloride or butyl acetate, may alternatively be used.

The organic solution is evaporated to dryness and the residue is defatted, either by chromatography, e.g. on silica gel with chloroform containing a small amount of methanol, e.g. at a ratio of 98:2, or by distribution between petroleum ether and methanol which has been mixed with an amount of water sufficing for a phase separation. In the first case the fractions which are antibiotically active against *Aspergillus niger* are combined, evaporated to dryness, and the residue is chromatographed in methanolic solution on Sephadex LH 20. In the second case the methanolic aqueous phase is concentrated, optionally after the addition of a further amount of water, to such an extent that the major portion of the methanol is distilled off, whereupon the aqueous mixture is extracted with ethylene chloride or another one of the above mentioned water-immiscible solvents, the resulting organic solution is evaporated to dryness, and the residue is chromatographed in methanolic solution on Sephadex LH 20. The further separation and purification of the two antibiotics is effected by repeated chromatography on aluminium oxide or silica gel or by the successive use of both adsorbents.

A further convenient method comprises the extraction of the culture liquor obtained from cultivation of the fungus strain NRRL 8044 with a water-immiscible solvent, optionally after previous mechanical comminution. Ethylene chloride is preferably used as solvent, but chloroform, ethyl acetate, methylene chloride or butyl acetate may alternatively be used. The organic phase is separated, dried and concentrated by evaporation. The residue is chromatographed, preferably with a methanol solution on Sephadex LH 20, whereby the fractions being active against *Aspergillus niger* are combined and again chromatographed on aluminium oxide with toluene to which 10–50% of ethyl acetate have been added. The detection of the active antibiotics is again effected by testing the activity against *Aspergillus niger*. Purification of the two antibiotics is effected by further chromatography.

For the production of the new antibiotics, it is likewise possible to use other strains obtained, for example, by selection or mutation by ultraviolet or X-ray irradiation, or by other measures, for example by treatment of laboratory cultures with suitable chemicals.

The above-mentioned strains NRRL 5760 and 8044 are already available to the public from the above-mentioned United States Department of Agriculture depository and also from the patentees and will continue to be available as working strains throughout the effective life of any patent issuing hereon. Any restrictions on the availability of the above-mentioned strains to the public have already been irrevocably removed.

In the following non-limitative Examples all temperatures are indicated in degrees Centigrade. Unless indicated otherwise all values mentioned herein are subject to the usual experimental error.

"Polygram" is a Trade Mark for plastic foil supports for silica gel suitable for thin layer chromatography.

"Sephadex LH 20" is a Trade Mark for silica gel suitable for column chromatography.

EXAMPLE 1

10 liters of a nutrient solution (of which each liter contains 30 g of sucrose, 10 g of Corn steep, 3 g of $NaNO_3$, 1 g of $K_2HPO_4$, 0.5 g of $MgSO_4.7H_2O$, 0.5 g of KCl and 0.01 g of $FeSO_4.7H_2O$) are inoculated with 100 cc of a conidia and mycelium suspension of the strain NRRL 5760, and incubation is effected in 700 cc penicillin flasks at 27° for 11 days.

The mycelium, which has been separated from the culture liquid, is extracted in a Turrax apparatus by crushing and stirring with 3.5 liters of 90% methanol, and the crushed mycelium, which is separated from the solvent by filtering with suction, is again treated twice in the same manner with 90% methanol. The combined filtrates are concentrated by evaporation in a vacuum at a bath temperature of 40° to such an extent that the vapour mainly consists of water alone. The resulting mixture is extracted six times with the same volume of ethylene chloride by shaking, whereupon the combined ethylene chloride solutions are purified by extraction with water and are concentrated by evaporation in a vacuum at a bath temperature of 40°. The resulting residue is chromatographed on 250 g of silica gel (silica gel 60 "Merck", grain size 0.063–0.200 mm), using chloroform containing 2% of methanol as eluant, and is collected in 200 cc fractions. The fractions which are antibiotically active against *Aspergillus niger* in the plate diffusion test are combined, evaporated to dryness as described above, and after dissolving in methanol are chromatographed on 110 g of Sephadex LH 20 with the same solvent, whereupon those 20 cc fractions showing an antibiotic effect against *Aspergillus niger* in the test indicated above, are combined. A test in the thin layer chromatogram, e.g. with silica gel on "Polygram" foils and hexane/acetone (1:1) as eluant, indicates that the residue of the methanol solution evaporated as described above mainly consists of the two new antibiotics S 7481/F-1 and S 7481/F-2. These are separated and simultaneously purified by a further chromatography of the mixture thereof, using a 1000-fold amount of silica gel of the above indicated quality and chloroform containing 2% of methanol. A testing of the eluate fractions, having a volume in milliliters which is half as large as the weight of the silica gel in grams, in the thin layer chromatogram, indicates that the antibiotic S 7481/F-1 appears first in the eluate, followed by a mixture of the two antibiotics and finally by homogeneous S 7481/F-2. Further amounts of the two antibiotics may be obtained from the mixture by repeating chromatography under the same conditions.

The new antibiotic S 7481/F-1 may be characterized as follows, when in amorphous form:

Colourless powder having an M.P. of ca 137°–140° (decomp.); $[\alpha]_D^{20} = -236°$ ($CHCl_3$, c=0.5); UV spectrum: see FIG. 1; IR spectrum: see FIG. 2; proton nuclear magnetic resonance: see FIG. 3; $^{13}C$ nuclear magnetic resonance: see Table.

Mass spectrum (CEC mass spectrograph 21-110B, source of ions E.B., admission system: direct, electron energy: 70 eV, ion acceleration: 4 kV, temperature ion source: 290°, pressure: $5.10^{-6}$ mm Hg, peak matching process, reference substance "PCR 8" [Tris-pentadecafluoroheptyl-1,3,5-triazine, M=1184.9374]: highest mass peak m/e=1183.831 ($\pm 0.004$), corresponding to the mass of the ion $C_{62}H_{109}N_{11}O_{11}$, the product of elimination of water from the molecule $C_{62}H_{111}N_{11}O_{12}$.

Solubility: readily soluble in most of the usual organic solvents, practically insoluble in petroleum ether and water. Behaviour in thin layer chromatogram (substance spots made visible with iodine vapour):

(a) Silica gel on glass plates; chloroform+4% of methanol as eluant: Rf=0.52.

(b) Silica gel on "Polygram" foils; hexane/acetone 1:1 as eluant: Rf=0.37; chloroform/acetone 2:1 as eluant: Rf=0.34.

Elementary analysis (sample dissolved in benzene, solution evaporated to dryness, residue dried in a high vacuum at 100° for 5 hours): found C 61.8, H 9.4, N 13.0, O 15.7%.

The values found are in agreement with the empirical formula $C_{62}H_{111}N_{11}O_{12}$.

The amino acids alanin, α-aminobutyric acid, N-methylleucin, N-methylglycin and valin may be detected in the hydrolysis product obtained by boiling the compound S 7481/F-1 with 6 N hydrochloric acid (20 hours).

The new antibiotic S 7481/F-2 may be characterized as follows, when in amorphous form:

Colourless powder having an M.P. of 127°–130° (decomp.); $[α]_D^{20} = -243°$ (chloroform, c=0.5); UV spectrum: see FIG. 4; IR spectrum: see FIG. 5; proton nuclear magnetic resonance: see FIG. 6. Mass spectrum (taken under the conditions as for antibiotic S 7481/F-1): highest mass peak m/e=1169.815 (±0.006), corresponding to the mass of the ion $C_{61}H_{107}N_{11}O_{11}$, the product of elimination of water from the molecule $C_{61}H_{109}N_{11}O_{12}$.

Solubility: readily soluble in most of the usual organic solvents, practically insoluble in petroleum ether and water. Behaviour in the thin layer chromatogram (substance spots made visible with iodine vapour):

(a) silica gel on glass plates; chloroform+4% of methanol as eluant: Rf=0.46.

(b) Silica gel on "Polygram" foils; hexane/acetone 1:1 as eluant: Rf=0.28; chloroform/acetone 2:1 as eluant: Rf=0.26.

Elementary analysis (sample dried in a high vacuum at 100° for 5 hours): found C 61.7, H 9.1, N 13.1, O 16.5%.

The values found are in agreement with the empirical formula $C_{61}H_{109}N_{11}O_{12}$.

The conidia and mycelium suspension used as starting material for the inoculation is produced from a culture of the originally isolated strain NRRL 5760, which is cultivated for 10 days on an agar medium, of which each liter contains 20 g of malt extract, 20 g of agar, 4 g of yeast extract, and demineralized water. The conidia and the mycelium are taken up in a physiological common salt solution. This suspension is used for the inoculation of the above nutrient solution.

EXAMPLE 2

250 liters of a nutrient solution (of which each liter contains 30 g of sucrose, 10 g of Corn steep, 3 g of NaNO$_3$, 1 g of K$_2$HPO$_4$, 0.5 g of MgSO$_4$.7H$_2$O, 0.5 g of KCl and 0.01 g of FeSO$_4$.7H$_2$O) are inoculated with 2.5 liters of a conidia and mycelium suspension of the strain NRRL 5760, and are incubated in 700 cc penicillin flasks at 27° for 11 days.

The mycelium is separated from the culture liquid by centrifuging and is homogenized in an Ultraturrax apparatus with 80 liters of 90% methanol, whereupon the methanolic extract solution is separated from the solid material by centrifuging, and the solids are again extracted twice in the same manner with 90% methanol. The combined extract solutions are concentrated to 15 liters in a vacuum at 30°–40°. The resulting aqueous phase is extracted 8 times with the same volume of ethylene chloride. Each of the ethylene chloride extracts is washed with 5 liters of water. The ethylene chloride solutions are combined and are then concentrated by evaporation in a vacuum at 30°–40°. Defatting is effected by dividing the extract residue between petroleum ether and 90% methanol in such a manner that after dissolution in 2 liters of 90% methanol it is successively shaken 3 times with 2 liter amounts of petroleum ether (B.P. 30°–35°) in three separatory funnels, whereupon the three petroleum ether phases are again successively extracted twice with 2 liter amounts of 90% methanol. 3 liters of water are added to the combined methanolic solutions, and the mixture is concentrated at 30°–40° to a volume of 2 liters. The aqueous concentrate is extracted by shaking 5 times with 2 liters of ethylene chloride; the ethylene chloride solutions are washed with 0.5 liter amounts of water, are combined and evaporated to dryness in a vacuum at 30°–40°. The residue is subjected to chromatography on a 25-fold volume of Sephadex LH 20, whereby methanol is used as eluant. The eluate is collected in 250 cc fractions; those fractions exhibiting an antibiotic effect against *Aspergillus niger* in the plate diffusion test are combined and evaporated to dryness in a vacuum at 30–40°. The residue is subsequently chromatographed on a 70-fold quantity of aluminium oxide (neutral) of activity 1, whereby mixtures of toluene and ethyl acetate are used for elution. The first ten fractions (volume of the fractions: half as much liters as adsorbent in kg), eluted with toluene containing 15% of ethyl acetate, first show the major amount of the antibiotic S 7481/F-1, followed by a mixture of S 7481/F-1 and S 7481/F-2. A further amount of the same mixture, containing a small amount of foreign matter, may be obtained by subsequent elution with toluene/ethyl acetate (1:1). The detection of the antibiotics in the eluate fractions is effected by thin layer chromatography e.g. with silica gel on "Polygram" foils and hexane/acetone (1:1) as eluant. The antibiotic S 7481/F-1 is obtained from the combined fractions containing the antibiotic S 7481/F-1 in homogeneous form, by evaporating in a vacuum at 30°–40° and subsequent drying of the residue in a high vacuum at 50°. The combined eluate fractions, containing the mixture, are also evaporated under the same conditions. For the obtention of a further amount of antibiotic S 7481/F-1 and of homogeneous S 7481/F-2, the residue is subjected to chromatography on a 1000-fold amount of silica gel, whereby chloroform containing 2% of methanol is used as eluant, proceeding in a manner analogous to that described in Example 1.

EXAMPLE 3

500 liters of nutrient solution (of which each liter contains 40 g of glucose, 5 g of casein peptone, 5 g of MgSO$_4$.7H$_2$O, 2 g of KH$_2$PO$_4$, 3 g of NaNO$_3$, 0.5 g of KCl, 0.01 g of FeSO$_4$, and demineralized water) are inoculated with 50 liters of a preculture of the strain NRRL 8044, and incubated in a steel fermenter at 27° for 13 days while stirring (170 revolutions/minute) and aerating (1 liter of air/minute/liter of nutrient solution).

500 liters of culture liquid are crushed with an Ultraturrax apparatus and extracted several times with 500 liter amounts of 1,2-dichloroethane. The organic phase is separated, dried over sodium sulphate and concentrated by evaporation in a vacuum. The evaporation residue is chromatographed on a 100-fold quantity of Sephadex LH 20 with methanol. The fractions which are active against *Aspergillus niger* are combined, and the mixture is chromatographed on a 100- to 200-fold quantity of neutral aluminium oxide (activity 1). Elution is effected with toluene to which 10–50% of ethyl acetate have been added. By-products are chiefly eluted first, then S 7481/F-1, and finally S 7481/F-2. Detection of the active antibiotics in the fractions is again effected by testing the activity against *Aspergillus niger*; purity is tested by thin layer chromatography on silica gel plates with chloroform/methanol (96:4), whereby the antibiotics are made visible with iodine vapour. The pure fractions are combined and triturated with hexane, whereby the antibiotics S 7481/F-1 and S 7481/F-2 are obtained in the form of a white amorphous powder, which is dried in a high vacuum at 50°.

The preculture used as starting material is obtained as follows:

The spore and mycelium suspension used for inoculation is produced from a culture of the originally isolated strain NRRL 8044, which is cultivated for 21 days at 27° on an agar medium (of which each liter contains 20 g of malt extract, 20 g of agar, 4 g of yeast extract, and demineralized water). The spores and the mycelium of this culture are taken up in a physiological common salt solution.

This suspension is used for inoculation of 50 liters of a nutrient solution having the same composition as the contents of the 500 liter steel fermenter, and incubation is effected in a steel fermenter at 27° for 3 days while stirring (200 revolutions/minute) and aerating (1 liter of air/minute/liter of nutrient solution). This fermentation solution is used as inoculating material for the 500 liter steel fermenter.

EXAMPLE 4

Amorphous S-7481/F-1 obtained from Example 1 may be crystallized from a 2 to 3 times amount of acetone at −15°, yielding white prismatic needles of m. pt. 148°–151° C.; $[\alpha]_D^{20} = -244°$ (c=0.6 in chloroform) and $[\alpha]_D^{20} = -189°$ (c=0.5 in methanol).

Analysis: C, 61.8%; H, 9.5%; N, 12.6%; O, 15.8%.

Table $^{13}$C spectra data of S 7481/F-1; 250 mg in 1.5 cc of CDCl$_3$; Bruker HX-90E; Sweep-width 6000 Hz.

| Address | Frequency [hz] | δ [ppm] | Intensity |
|---|---|---|---|
| 1260 | 3915.5273 | 173.0237 | 184 |
| 1264 | 3909.6679 | 172.7648 | 192 |
| 1293 | 3867.1875 | 170.3876 | 91 |
| 1299 | 3858.3984 | 170.4992 | 215 |
| 1312 | 3839.3554 | 169.6577 | 207 |
| 1317 | 3332.0312 | 169.3341 | 268 |
| 1937 | 2923.8281 | 129.2014 | 220 |
| 1992 | 2843.2617 | 125.6412 | 225 |
| 2745 | 1740.2343 | 76.8994 | 20 |
| 2785 | 1681.6406 | 74.3102 | 165 |
| 3027 | 1327.1484 | 58.6455 | 187 |
| 3042 | 1305.1757 | 57.6745 | 223 |
| 3047 | 1297.8515 | 57.3500 | 253 |
| 3051 | 1291.9921 | 57.0920 | 40* |
| 3081 | 1248.0468 | 55.1501 | 844 |
| 3159 | 1133.7890 | 50.101 | 172 |
| 3184 | 1097.1679 | 48.4828 | 566 |
| 3189 | 1089.8437 | 48.1592 | 276 |
| 3239 | 1016.6015 | 44.9227 | 206 |
| 3305 | 919.9128 | 40.6505 | 158 |
| 3327 | 837.6953 | 39.2264 | 192 |
| 3332 | 880.8710 | 38.9028 | 222 |
| 3357 | 843.7500 | 37.2845 | 167 |
| 3363 | 834.9609 | 36.8961 | 30* |
| 3380 | 810.0585 | 35.7957 | 567 |
| 3387 | 799.8046 | 35.3426 | 304 |
| 3411 | 764.6484 | 33.7891 | 182 |
| 3449 | 703.9843 | 31.3294 | 167 |
| 3454 | 701.6601 | 31.0057 | 518 |
| 3475 | 670.8984 | 29.6464 | 544 |
| 3478 | 666.5039 | 29.4522 | 179 |

Table-continued $^{13}$C spectra data of S 7481/F-1; 250 mg in 1.5 cc of CDCl$_3$; Bruker HX-90E; Sweep-width 6000 Hz.

| Address | Frequency [hz] | δ [ppm] | Intensity |
|---|---|---|---|
| 3486 | 654.7851 | 28.9343 | 310 |
| 3543 | 571.2890 | 25.2447 | 287 |
| 3549 | 562.5000 | 24.8563 | 631 |
| 3553 | 556.6406 | 24.5974 | 843 |
| 3566 | 537.5976 | 23.7559 | 1000 |
| 3574 | 525.8789 | 23.2381 | 762 |
| 3582 | 514.1601 | 22.7202 | 58* |
| 3596 | 493.6523 | 21.8140 | 606 |
| 3607 | 477.5390 | 21.1020 | 231 |
| 3622 | 455.5664 | 20.1310 | 165 |
| 3628 | 446.7773 | 19.7427 | 254 |
| 3645 | 421.8750 | 18.6422 | 285 |
| 3650 | 414.5507 | 18.3186 | 314 |
| 3654 | 408.6914 | 18.0597 | 278 |
| 3658 | 402.8320 | 17.8007 | 277 |
| 3674 | 379.3945 | 16.7651 | 224 |
| 3638 | 358.8867 | 15.8588 | 202 |
| 3751 | 222.6562 | 9.8389 | 139 |
| 3933 | 0.0000 | 0.0000 | 111 = tetramethylsilane |

*Registered signals of CDCl$_3$ and resonances

S 7481/F-1 and S 7481/F-2 are useful because they exhibit pharmacological activity in animals. In the case of S 7481/F-1 (Cyclosporin A), this pharmacological activity has been reported in J. F. Borel et al., Agents and Actions 6, 468–475 (1976), the contents of which are incorporated herein by reference.

The antibiotics S 7481/F-1 and S 7481/F-2 are useful as antibiotic agents, as indicated by standard tests, for example by inhibition of the growth of *Asperigillus niger*.

The antibiotics are furthermore useful as arthritis-inhibitors, e.g. for the treatment of chronic rheumatoid arthritis, as indicated in standard tests, e.g. by an inflammation-inhibiting effect at doses of 10 to 50 mg/kg animal body weight in the Freund's adjuvant arthritis latent period test in rats, and at doses of 50 mg/kg animal body weight in the Freund's adjuvant arthritis therapy in rats.

S 7481/F-1 and S 7481/F-2 are furthermore useful as immunosuppressives, e.g. by their effect on humoral and cellular immunity, as indicated in standard tests. Thus they are useful in the suppression of the formation of, or proliferation of, immunocytes or lymphocytes, and are therefore useful in the treatment of autoimmune diseases, suppressing the rejection of transplants, e.g. organ transplants such as skin, bone narrow and kidney transplants. The effects of the compounds are ascertained in the tests described in the above article by J. F. Borel et al., and in particular in the following tests.

(a) Local hemolysis in gel Jerne test:

The inhibition of hemolytic plaque forming cells in % as compared with the controls is 99% at a dose of 2×60 mg/kg i.p., 90% at a dose of 1×150 mg/kg p.o., and 99.5% at a dose of 3×200 mg/kg p.o. The formation of both immunoglobulin antibodies and immunoglobulin G$_{2a}$ antibodies is inhibited.

(b) Hemagglutination test (HAT) in mice:

The antibodies formed against sheep erythrocytes are detected. The inhibition is expressed in the suppressive index (SI), whereby the untreated controls are indicated by 1.00; SI=0.5 after 5×200 mg/kg p.o.

(c) Skin transplantation test in mice:

The prolongation of the period of survival of the skin graft in H-2 histoin compatible mice is significantly prolonged after a dose of 10×200 mg/kg p.o., as compared with the untreated control animals: about 16 days longer than the controls.

(d) Experimental allergic encephalomyelitis (EAE) in rats:

The experimentally induced nerve tissue damages paralyze 8 of 10 animals in the untreated control animals, but in the case of the same number of test animals treated with 13×25 mg/kg i.p., a 100% protection is ascertained.

(e) Oxazolone test in mice:

The decrease of ear swelling is expressed as suppressive index (SI); SI=0.6 after 5×70 mg/kg p.o.

(f) Cytopenias in the bone marrow and blood:

The high oral administration of 6×500 mg/kg does not show any significant depression of the blood-forming cells in the bone marrow nor a hypoleukocytosis in the blood on the 1st, 3rd and 7th day after the last administration of the compound.

For all the above-mentioned uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 900 mg, and dosage forms suitable for oral administration comprise from about 12 mg to about 450 mg of the compounds admixed with a solid or liquid pharmaceutical carrier or diluent.

The present invention also provides a pharmaceutical composition comprising antibiotic S7481/F-1 or S7481/F-2 in pure form or as a pharmaceutically acceptable crude concentrate in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

We claim:

1. A process for the production of S7481/F-1 of formula I, or S7481/F-2 of formula II, or S7481/F-1 and S7481/F-2, which comprises cultivating a S7481/F-1; S7481/F-2, or S7481/F-1 and S7481/F-2 producing strain of the fungus species, *Cylindrocarpon lucidum* Booth or *Trichoderma polysporum* (Link ex Pers.) Rifai (now referred to as *Tolypocladium inflatum* Gams) in contact with a nutrient medium and isolating S7481/F-1; S7481/F-2 or S7481/F-1 and S7481/F-2.

2. A process according to claim 1, wherein the strain is a *Cylindrocarpon lucidum* Booth strain.

3. A process according to claim 2, wherein the strain is NRRL 5760 an obvious taxonomical equivalent thereof, or a mutant or variant thereof.

4. A process according to claim 3, wherein the strain is NRRL 5760 or an obvious taxonomical equivalent thereof.

5. A process according to claim 1, wherein the strain is a *Trichoderma polysporum* (Link ex Pers.) Rifai strain.

6. A process according to claim 5, wherein the strain is NRRL 8044 or an obvious taxonomical equivalent thereof, or a mutant or variant thereof.

7. A process according to claim 6, wherein the strain is NRRL 8044 or an obvious taxonomical equivalent thereof.

8. A process according to claim 1 for the production of antibiotic S 7481/F-1 having the following characteristics when in amorphous form:

colorless powder; M.P. 148°–151° C. (decomp.); $[\alpha]_D^{20} = -236°$ (CHCl$_3$; c=0.5);
U.V. Spectrum [CH$_3$OH; c=1.063 g/l; d=0.01 cm] as shown in FIG. 1 of the accompanying drawings;
I.R. Spectrum [CH$_2$Cl$_2$] as shown in FIG. 2 of the accompanying drawings;
Proton N.M.R. Spectrum [90 MHz; CDCl$_3$] as shown in FIG. 3 of the accompanying drawings;
Carbon-13 N.M.R. Spectrum [250 mg in 1.5 ml CDCl$_3$; sweep width 6000 MHz] as shown in accompanying Table;
High resolution mass spectrum [ion acceleration 4 kv; temperature ion source 290° C.; pressure 5.10$^{-6}$ mm Hg] peak of highest mass=m/e 1183.831 [±0.004] corresponding to C$_{62}$H$_{109}$N$_{11}$O$_{11}$ recognizable as product of elimination of water from C$_{62}$H$_{111}$N$_{11}$O$_{12}$;
Elementary analysis C 61.8, H 9.4, N 13.0, O 15.7% in agreement with empirical formula C$_{62}$H$_{111}$N$_{11}$O$_{12}$;

and release of amino acids alanine, α-aminobutyric acid, N-methylleucine, N-methylglycine and valine on reaction with 6 N aqueous hydrochloric acid at reflux, which comprises cultivating a S 7481/F-1; S7481/F-2, or S 7481/F-1 and S 7481/F-2 producing strain of the fungus species, *Cylindrocarpon lucidum* Booth or *Trichoderma polysporum* (Link ex Pers.) Rifai (now referred to as *Tolypocladium inflatum* Gams) in contact with a nutrient medium and separating S 7481/F-1 from S 7481/F-2.

9. A process according to claim 1 for the production of antibiotic S 7481/F-2 having the following characteristics when in amorphous form:

Colorless powder; M.P. 127°–130° C. (decomp.); $[\alpha]_c^{20} = -243°$ (CHCl$_3$, c=0.5);
U.V. Spectrum [CH$_3$OH; c=1.062 g/l; d=0.01 cm] as shown in FIG. 4 of the accompanying drawings;
I.R. Spectrum [CH$_2$Cl$_2$] as shown in FIG. 5 of the accompanying drawings;
Proton N.M.R. Spectrum [90 MHz; CDCl$_3$] as shown in FIG. 6 of the accompanying drawings;
High resolution mass Spectrum [ion acceleration 4 kv; ion source temperature 290° C.; pressure 5.10$^{-6}$ mm Hg] peak of highest mass m/e 1169.815 (±0.006) corresponding to C$_{61}$H$_{107}$N$_{11}$O$_{11}$, the product of water elimination from C$_{61}$H$_{109}$N$_{11}$O$_{12}$; and
Elementary analysis found C 61.7; H 9.1, N 13.1, O 16.5% in agreement with empirical formula C$_{61}$H$_{109}$N$_{11}$O$_{12}$, which comprises cultivating a S 7481/F-1; S 7481/F-2, or S 7481/F-1 and S 7481/F-2 producing strain of the fungus species, *Cylindrocarpon lucidum* Booth or *Trichoderma polysporum* (Link ex Pers.) Rifai (now referred to as *Tolypocladium inflatum* Gams) in contact with a nutrient medium and separating S 7481/F-2 from S 7481/F-1.

* * * * *

UNITED STATES PATENT AND TRADEMARK OFFICE
CERTIFICATE OF CORRECTION

PATENT NO. : 4,215,199  Page 1 of 2
DATED : July 29, 1980
INVENTOR(S) : EUGEN HARRI/ARTUR RUEGGER It is certified that error appears in the above—identified patent and that said Letters Patent is hereby corrected as shown below:

Col. 2, lines 17-20 and Col. 12, lines 16-19, delete in both instances the portion of the formula on the right-hand side having the structure:

and insert in its place in both instances:

UNITED STATES PATENT AND TRADEMARK OFFICE
CERTIFICATE OF CORRECTION

PATENT NO. : 4,215,199

DATED : July 29, 1980

INVENTOR(S) : EUGEN HARRI/ARTUR RUEGGER

It is certified that error appears in the above—identified patent and that said Letters Patent is hereby corrected as shown below:

Signed and Sealed this

Thirtieth Day of November 1982

|SEAL|

Attest:

Attesting Officer

GERALD J. MOSSINGHOFF

Commissioner of Patents and Trademarks

UNITED STATES PATENT AND TRADEMARK OFFICE
Certificate

Patent No. 4,215,199                                                Patented July 29, 1980

Eugene Harri and Artur Ruegger

Application having been made by Eugene Harri and Artur Ruegger, the inventors named in the patent above-identified, and Sandoz Ltd., the assignee, for the issuance of a certificate under the provisions of Title 35, Section 256, of the United States Code, adding the names of Zoltan Kis and Hans Tscherter as joint inventors, and a showing and proof of facts satisfying the requirements of the said section having been submitted, it is this 28th day of Feb. 1984, certified that the names of the said Zoltan Kis and Hans Tscherter are hereby added to the said patent as joint inventors with the said Eugene Harri and Artur Ruegger.

Fred W. Sherling,
*Associate Solicitor.*